United States Patent [19]

Hell et al.

[11] Patent Number: 5,504,791
[45] Date of Patent: Apr. 2, 1996

[54] ANNULAR ANODE X-RAY COMPUTED TOMOGRAPHY APPARATUS WITH A SINGLE MAGNET SYSTEM FOR GUIDING AND DEFLECTING THE ELECTRON BEAM

[75] Inventors: Erich Hell, Erlangen; Manfred Fuchs, Nuremberg, both of Germany

[73] Assignee: Siemens Aktiengesellschaft, Munich, Germany

[21] Appl. No.: 378,254

[22] Filed: Jan. 24, 1995

[30]  Foreign Application Priority Data

Mar. 18, 1994 [DE]  Germany .......................... 44 09 365.9

[51] Int. Cl.[6] ..................................................... H05G 1/64
[52] U.S. Cl. ............................................ 378/10; 378/137
[58] Field of Search ............................... 378/10, 137, 4, 378/12, 113, 138, 121

[56]  References Cited

U.S. PATENT DOCUMENTS 5,172,401  12/1992  Asari et al. ............................ 378/10
5,197,088  3/1993  Vincent et al. ....................... 378/10
5,247,556  9/1993  Eckert et al. .

*Primary Examiner*—David P. Porta
*Attorney, Agent, or Firm*—Hill, Steadman & Simpson

[57]  ABSTRACT

In an electronic x-ray computed tomography apparatus that enables a scanning of approximately 360°, the electron beam is guided in an annularly fashioned magnet arrangement that has a U-shaped cross section. The U enables the guidance of the electron beam to the annular anode and enables the emergence of the x-radiation. The magnet arrangement is composed of a number of side-by-side U-shaped magnet elements arranged to form an annulus with a coil for excitation of the magnet element respectively arranged on the cross bar of each U. A single magnetic arrangement is thus used to generate both the electron beam guidance field and, by means of a sudden polarity reversal of a magnet element disposed at a desired deflection location, the deflection field.

11 Claims, 5 Drawing Sheets and # ANNULAR ANODE X-RAY COMPUTED TOMOGRAPHY APPARATUS WITH A SINGLE MAGNET SYSTEM FOR GUIDING AND DEFLECTING THE ELECTRON BEAM

BACKGROUND OF THE INVENTION

1. Field of the Invention

The present invention is directed to an x-ray computed tomography apparatus of the type wherein an annular anode is scanned by an electron beam to produce an x-ray beam which moves in a circular motion centered at the center of an examination region.

2. Description of the Prior Art

An x-ray computed tomography apparatus of the type described above, i.e., with electronic scanning of an annular anode, is disclosed in German OS 4 103 588. An especially fast scanning of an examination subject is possible with such a computed tomography apparatus, plus it has a low space requirement. A static guidance field that holds the electrons on the predetermined orbit and a dynamic deflection (kink) field that deflects the electrons onto the annular anode at the desired location are required for guiding and deflecting the electron beam. In the known x-ray computed tomography apparatus, only a scanning of less than 360° is possible because of the structural design, particularly of the guidance and deflection system.

SUMMARY OF THE INVENTION

An object of the present invention is to provide an x-ray computed tomography apparatus wherein an annular anode is scanned to produce an x-ray beam and wherein a scan angle of approximately 360° can be achieved.

This object is inventively achieved in a computed tomography apparatus constructed in accordance with the principles of the present invention wherein the electron beam guidance and kink fields are both generated by one magnet system. In the x-ray computed tomography apparatus of the invention, the same magnetic dipoles are used for generating the guidance magnetic field and the deflection magnetic field. Up to 100 separate magnet elements that are magnetically separated from one another are combined to form an annulus. The magnet elements can thereby be separately driven. The yoke of the magnet elements is either composed of a suitably rolled transformer sheet metal or of a ferrite core. The kinking of the electrons out of the orbit, i.e. their deflection onto the annular anode, ensues at the desired location by means of a sudden re-polarization of the magnetic field, at the desired location from the guidance mode into the kink mode.

DESCRIPTION OF THE PREFERRED EMBODIMENTS

Figure 1:
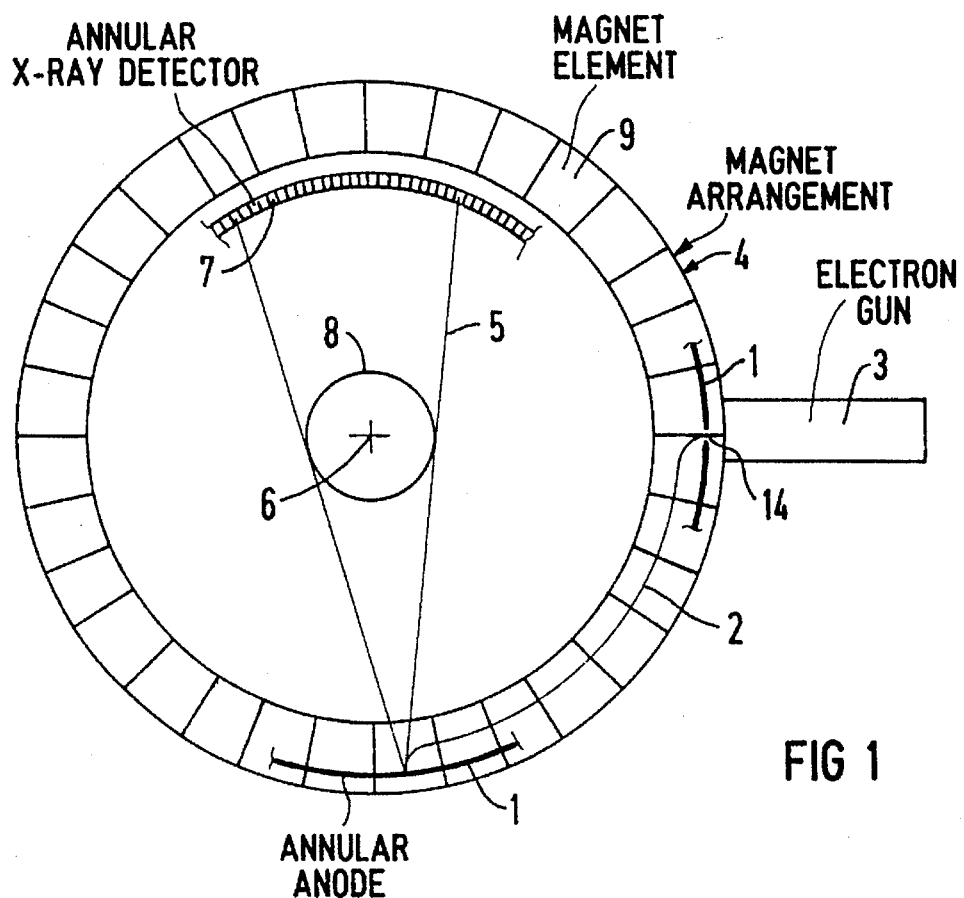
FIG. 1 illustrates the basic components of an x-ray computed tomography apparatus of the invention.
Figure 2:
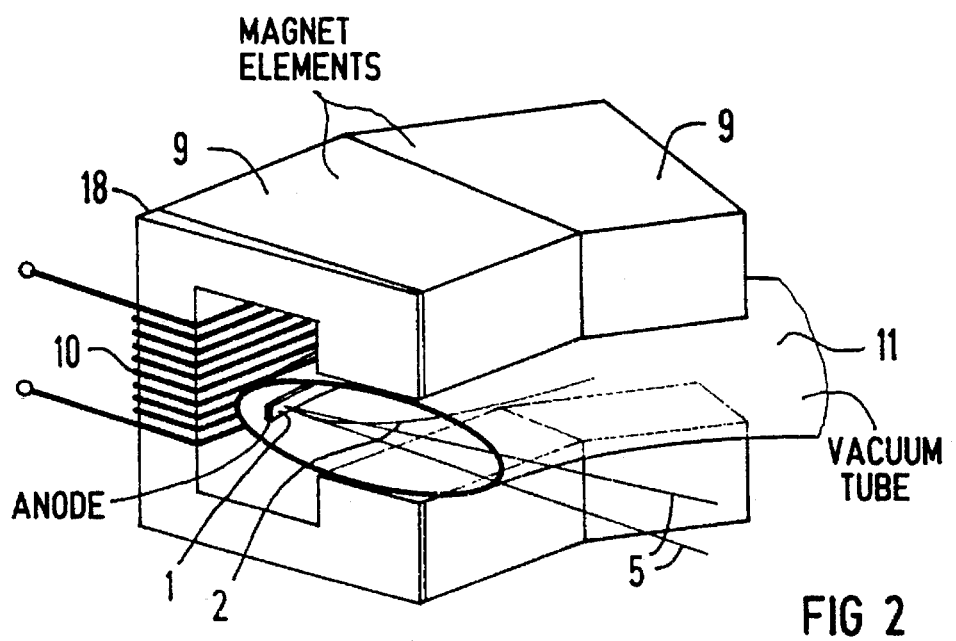
FIGS. 2 and 3 show respective views of the magnet elements of the x-ray computed tomography apparatus of FIG. 1.

The x-ray source of an x-ray computed tomography apparatus having an annular anode 1 is partially shown in FIG. 1. The anode 1 is contained inside an annular vacuum tube 11, as shown in FIG. 2. The annular anode I is scanned by an electron beam 2 that is generated by an electron gun 3. An annularly fashioned magnet arrangement 4 circularly guides the electron beam and deflects (kinks) it onto the annular anode 1. An x-ray beam 5 emanates from the respective focus (point of incidence of the electron beam 2 on the annular anode 1 ). This x-ray beam 5 is gated to form a fan-shaped beam in a known way and rotates around the system axis 6. It is incident on an annular radiation detector 7 that generates electrical signals corresponding to the received radiation intensity and supplies them to a computer that generates an image of a patient arranged in the measuring field 8 therefrom. So that the x-ray beam 5 is not impeded by the radiation detector 7 as it emerges from the vacuum tube 11 (FIG. 2) having an elliptical cross section, the radiation detector 7 is laterally arranged next to the exit window.

The magnet arrangement 4 is constructed of a plurality of magnet elements 9 that are joined to one another. According to FIG. 2, the magnet arrangement 4 has a U-shaped cross section, whereby the annular anode 1 proceeds in the inside of the vacuum tube 11, for example a metal tube having a Be window, and thus proceeds in the inside of the U and the electron beam 2 is guided in the U and the x-ray beam 5 emerges through the U.

Figure 3:
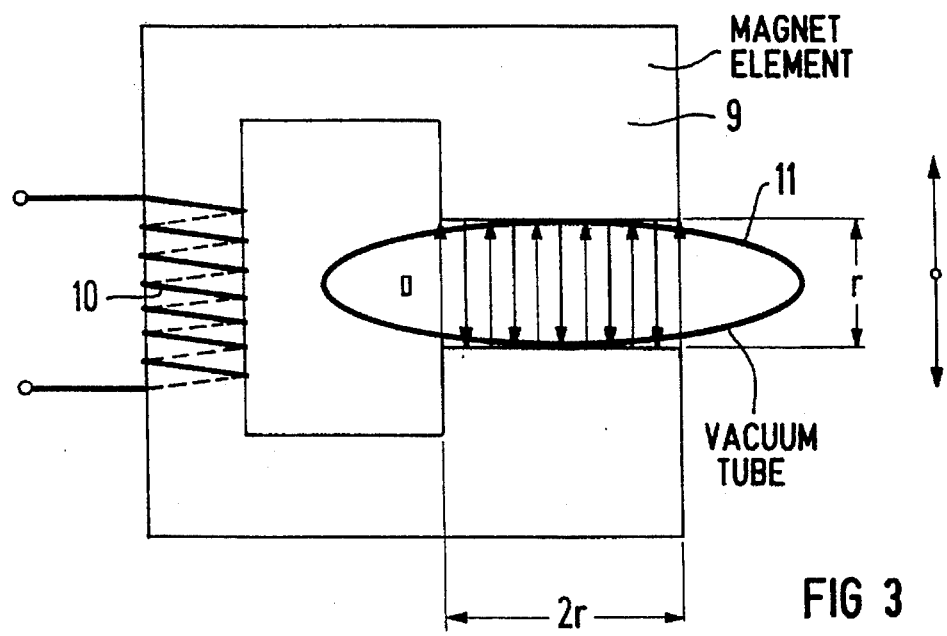

As shown in FIG. 3, each magnet element 9 carries a coil 10 for excitation on the crossbar of the U. The deflection (kinking) of the electrons from the circular orbit ensues at the desired location by means of a discontinuous re-polarization of the magnetic field within at least one magnet element at this location. The thin arrows in FIG. 3 represent the guidance field and the thick arrows represent the kink field. The guidance magnetic field and kink magnetic field are generated by the same magnet elements 9 that, according to FIG. 1, are annularly combined to form a full circle. The individual magnet elements 9 are each magnetically separated from one another by a suitable air gap. The switching from guidance mode into the kink mode ensues by a sudden re-polarization of the magnetic field with the assistance of a suitable electronics. The depth 2r of the pole shoe is at least twice as great as the pole shoe spacing r.

Figure 4:
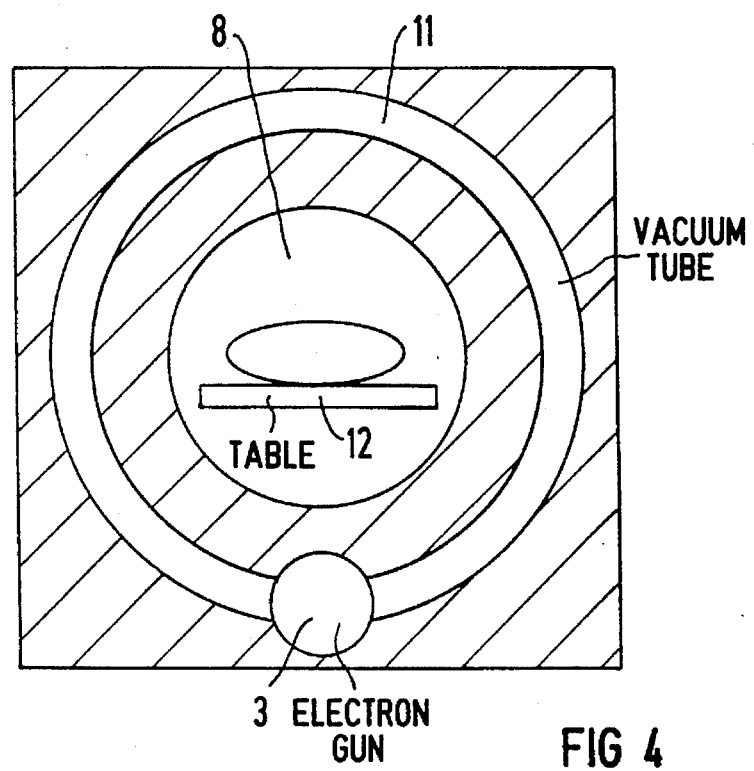
FIG. 4 is a sectional front view of an embodiment of the apparatus of FIG. 1 wherein the electron gun is contained within the gantry.
Figure 5:
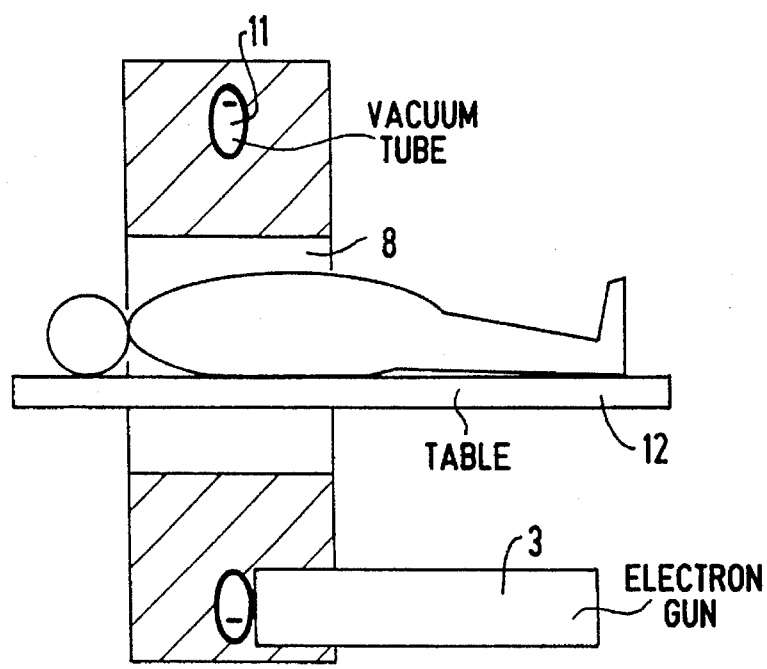
FIGS. 5 and 6 are side views of the apparatus of FIG. 4 showing that the gantry can be tilted together with the electron gun.
Figure 6:
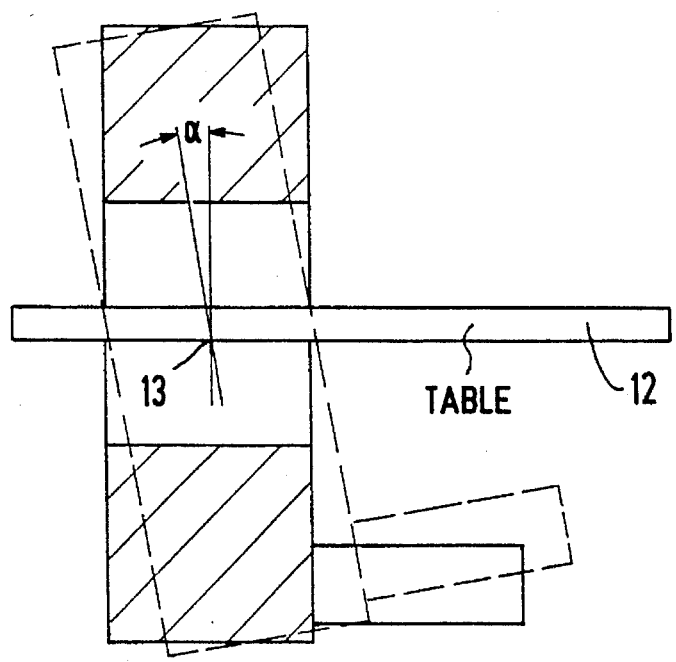

FIGS. 4–6 show two views of a version of the x-ray computed tomography apparatus of FIG. 1 wherein the electron gun 3 is axially connected by a flange to the evacuated, annular x-ray source 11 to which the magnet arrangement 9 according to FIG. 1 is allocated. The patient rests on a table 12. The x-ray source 11 together with the electron gun 3 can be tilted with the gantry around a horizontal axis 13 (FIG. 6). The tilt is possible with a low space requirement because the electron gun 3 is arranged under the table 12.

In the x-ray computed tomography apparatus of FIG. 1, a true 360° mode wherein the x-ray beam 5 can be rotated by 360° around the axis 6 is achieved when the electron beam 2 is radially injected between the first and the last magnet element 9 through a bore 14 present in the annular anode 1, is deflected by 90°, and proceeds through the entire magnet arrangement 4. The last magnet element 9 is axially tilted so that the electron beam 2 does not interact with the sides of the electron beam bore in the annular anode 1.

Figure 7:
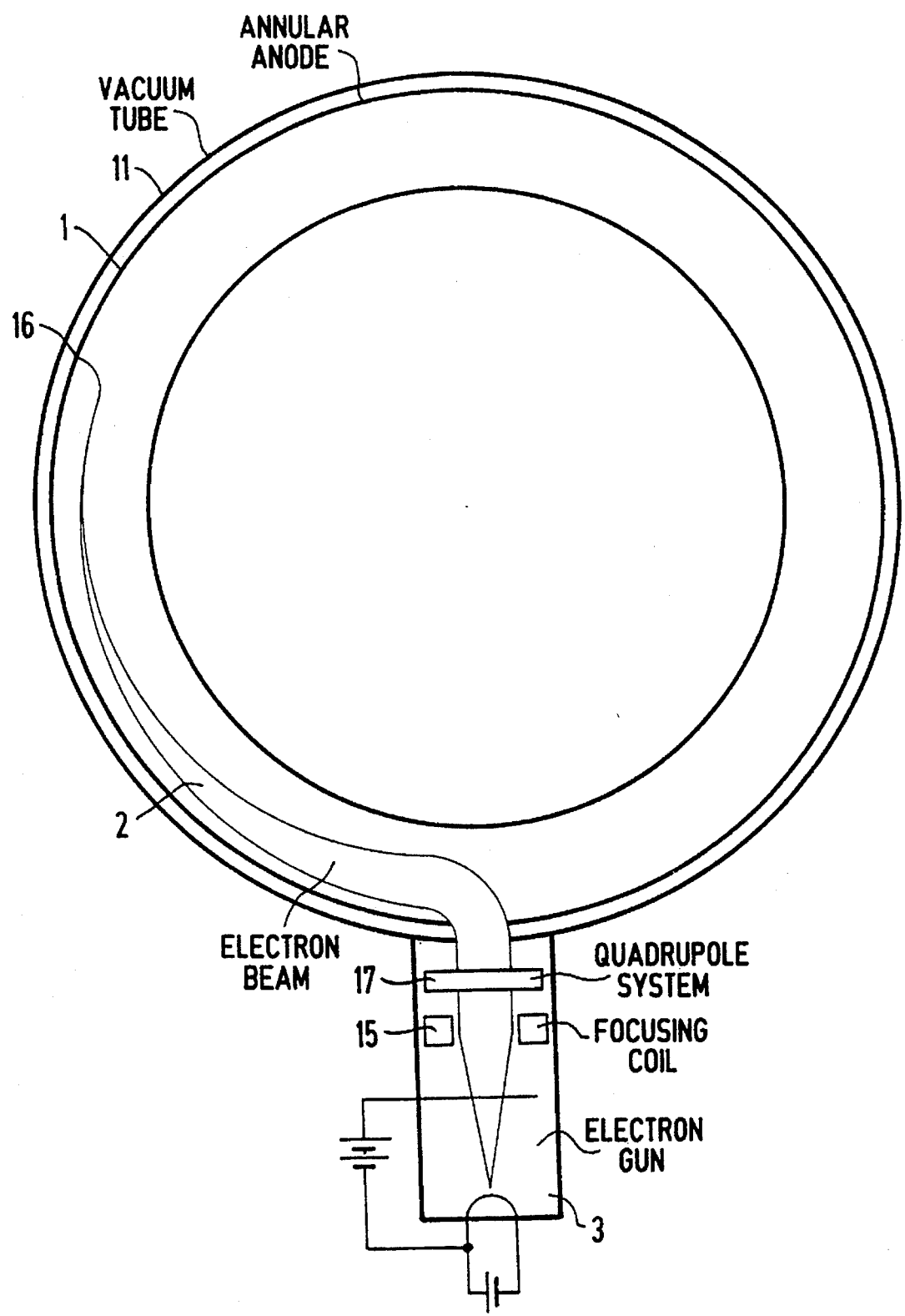
FIG. 7 shows a detail of the computed tomography apparatus of FIG. 1 for explaining the focusing.

The focusing of the electron beam 2 onto the annular anode 1 ensues dependent on the distance between the focusing coil 15 (FIG. 7) and the focus 16 on the annular anode 1 in such a way that the electron beam 2 is sharply adjusted at the focus 16.

A quadupole system 17 with which the intensity distribution of the electron beam 2 in the focus 16 can be maintained constant along the circumferential path of the annular anode 1 lies directly following the focusing coil 15.

The time for one revolution of the electron beam can lie between 50 ms and 20 ms, i.e., the orbital frequency varies between 20 Hz and 50 Hz. The magnet elements 9 are therefore preferably manufactured of a plurality of stacked, trapezoidally rolled, sheet metal transformer lamellae or of ferrite material (see, for example, the sheet metal lamella 18 in FIG. 2).

The pole shoe depth of the magnet element 9 (2r in FIG. 3) must be at least twice as deep as the spacing r between the two pole shoes because of the requirement for uniformity or homogeneity of the magnetic field. The cross section of the vacuum tube 11 should be an ellipse also because of the required uniformity or homogeneity of the magnetic field (FIG. 2).

Figure 8:
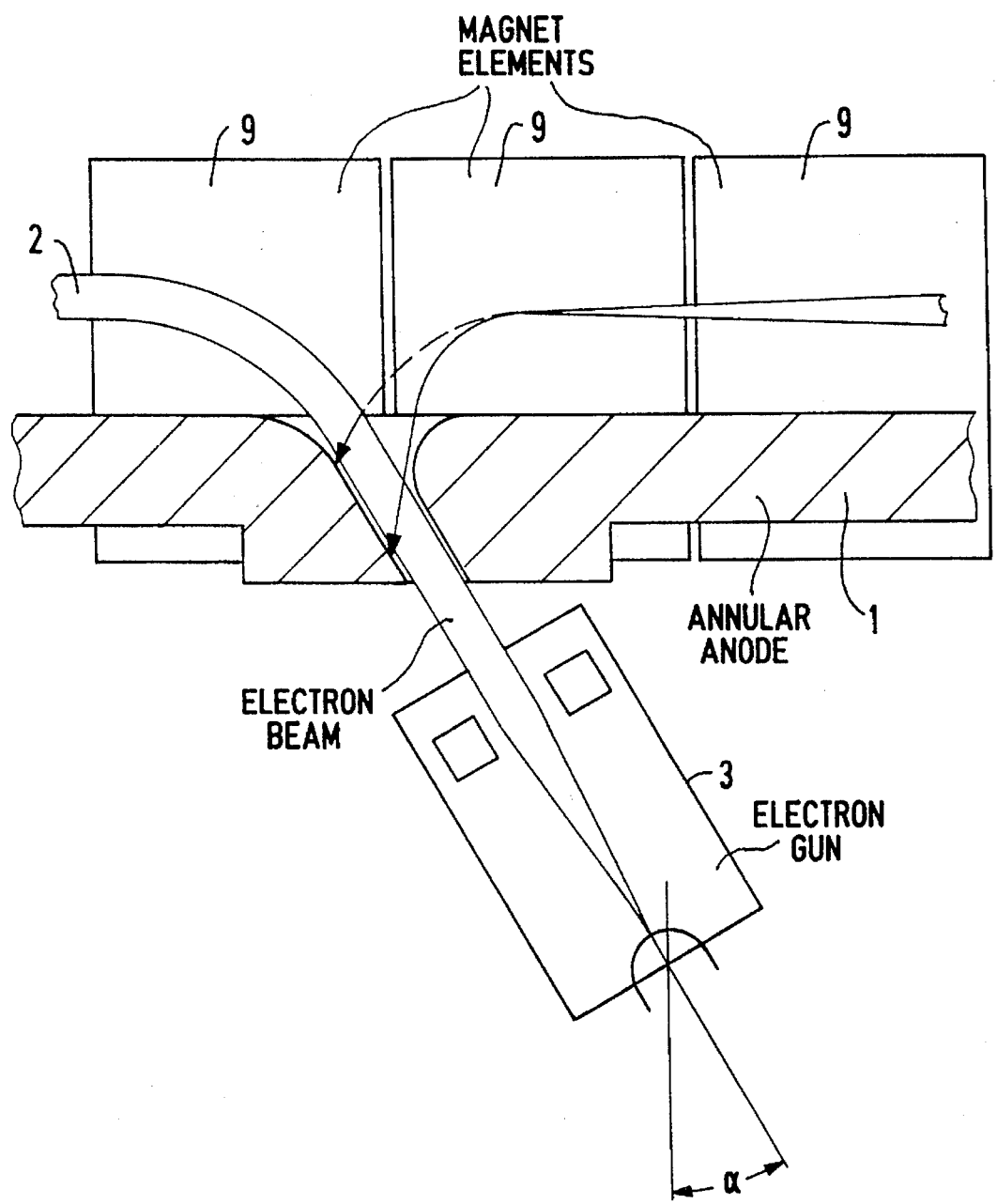
FIG. 8 shows a preferred arrangement of the electron gun for use in the x-ray computed tomography apparatus of the invention.

FIG. 8 shows that the electron gun 3 can enter into the vacuum tube through a bore in the annular anode 1 at an angle deviating from 90°. A 360° scanning is thus possible. It is thus also assured that the electron beam does not run back into the electron gun when it has passed through the vacuum tube 11.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray computed tomography apparatus comprising:
   an annular vacuum tube having an annular anode therein surrounding examination region;
   an electron gun which produces an electron beam; and
   a single magnet means for guiding said electron beam to scan said annular anode and for deflecting said electron beam, at successive, selected locations, onto said annular anode for producing an x-ray beam which rotates around said examination region, said single magnet means comprising a plurality of side-by-side magnet elements arranged to form an annulus, each magnet element having a U-shaped cross section with an open side and said annular tube and annular anode being disposed inside the U of each magnet element, each magnet element having a coil wound around it on a crossbar of the U, and means for controlling current flow through said coil for guiding said electron beam and for selectively producing a rapid reversal of polarity of said current flow for deflecting said electron beam onto said anode.

2. An x-ray computed tomography apparatus as claimed in claim 1 wherein said electron gun is oriented relative to said tube for emitting said electron beam radially into said tube at an angle deviating from 90°.

3. An x-ray computed tomography apparatus as claimed in claim 1 wherein said electron gun is oriented relative to said tube to emit said electron beam radially onto said anode.

4. An x-ray computed tomography apparatus as claimed in claim 1 further comprising a table for supporting an examination subject in said examination region, and wherein said electron gun is axially disposed beneath said table.

5. An x-ray computed tomography apparatus as claimed in claim I comprising means for operating each coil for focusing said electron beam onto said annular anode.

6. An x-ray computed tomography apparatus as claimed in claim 1 wherein said electron gun comprises quadupole means for maintaining an intensity distribution of said electron beam constant at a location on said annular anode at which said electron beam is incident on said annular anode.

7. An x-ray computed tomography apparatus as claimed in claim I wherein each magnet element comprises a plurality of stacked, trapezoidally rolled, sheet metal transformer lamellae.

8. An x-ray computed tomography apparatus as claimed in claim 1 wherein each magnet element is composed of ferrite material.

9. An x-ray computed tomography apparatus as claimed in claim 1 wherein each magnet element has a pole shoe depth and a pole shoe spacing, said pole shoe depth being at least twice as large as said pole shoe spacing.

10. An x-ray computed tomography apparatus as claimed in claim 1 further comprising means for tilting said tube and said electron gun around a horizontal axis.

11. An x-ray computed tomography apparatus as claimed in claim 1 wherein said tube has an elliptical cross section.

* * * * *